(12) United States Patent
Linares et al.

(10) Patent No.: US 9,289,303 B2
(45) Date of Patent: Mar. 22, 2016

(54) DYNAMIC INTERFACE SUPPORT ESTABLISHED BETWEEN A CERAMIC HIP JOINT BALL AND A SUPPORTING BALL STEM

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US); Ryan T. Greene, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 1 day.

(21) Appl. No.: 14/283,836

(22) Filed: May 21, 2014

(65) Prior Publication Data

US 2014/0350691 A1 Nov. 27, 2014

Related U.S. Application Data

(60) Provisional application No. 61/825,552, filed on May 21, 2013.

(51) Int. Cl.
*A61F 2/36* (2006.01)
*A61F 2/30* (2006.01)

(52) U.S. Cl.
CPC ............ *A61F 2/3609* (2013.01); *A61F 2/3607* (2013.01); *A61F 2002/30014* (2013.01); *A61F 2002/3021* (2013.01); *A61F 2002/30069* (2013.01); *A61F 2002/30179* (2013.01); *A61F 2002/30217* (2013.01); *A61F 2002/30235* (2013.01); *A61F 2002/30332* (2013.01); *A61F 2002/30405* (2013.01); *A61F 2002/30448* (2013.01); *A61F 2002/30474* (2013.01); *A61F 2002/30518* (2013.01); *A61F 2002/30563* (2013.01);

(Continued)

(58) Field of Classification Search
CPC ....... A61F 2/32; A61F 2/3607; A61F 2/3609; A61F 2002/30179; A61F 2002/30235; A61F 2002/30474; A61F 2002/365; A61F 2002/3652

See application file for complete search history.

(56) References Cited

U.S. PATENT DOCUMENTS 4,227,265 A * 10/1980 Frey ...................... A61F 2/3609
403/255
5,066,304 A * 11/1991 Crowninshield ...... A61F 2/3609
623/22.45

(Continued)

FOREIGN PATENT DOCUMENTS

FR 2290880 A1 * 6/1976 ............ A61F 2/3609
FR 2761878 A1 * 10/1998 ................ A61F 2/30

*Primary Examiner* — Marcia Watkins
(74) *Attorney, Agent, or Firm* — Dinsmore & Shohl LLP; Douglas J. McEvoy

(57) ABSTRACT

An artificial hip joint assembly including a ball mounted atop a supporting stem, the stem adapted to being mounted to a reconditioned end of a femur bone, with the ball adapted to seat within an acetabulum socket of a pelvic bone. An intermediate component is mounted between the ball and stem, the intermediate component incorporating force absorbing and redirecting properties at an engagement interface between the ball and stem in response to impact forces generated upon the ball by the pelvic bone. The intermediate component can be constructed of a softer material than either the ball or stem, the intermediate component can further include a sleeve exhibiting a plurality of interior threads and facilitating mounting of an exteriorly threaded end location of the stem.

9 Claims, 7 Drawing Sheets

(52) U.S. Cl.
CPC .................. *A61F2002/30565* (2013.01); *A61F 2002/30598* (2013.01); *A61F 2002/365* (2013.01)

(56) References Cited

U.S. PATENT DOCUMENTS

| | | | |
|---|---|---|---|
| 7,846,211 B2 | 12/2010 | Clifford et al. | |
| 8,202,323 B2 | 6/2012 | Wyss et al. | |
| 8,226,728 B2 * | 7/2012 | Preuss | A61F 2/34 623/22.14 |
| 8,709,090 B2 | 4/2014 | Makower et al. | |
| 8,715,358 B2 | 5/2014 | Masini | |
| 2004/0083003 A1 | 4/2004 | Wasielewski | |
| 2008/0275564 A1 | 11/2008 | Makower et al. | |
| 2009/0326669 A1 * | 12/2009 | Preuss | A61F 2/34 623/22.14 |
| 2010/0121457 A1 | 5/2010 | Clifford et al. | |
| 2012/0123551 A1 | 5/2012 | Landry et al. | |
| 2013/0282131 A1 | 10/2013 | Anapliotis et al. | |
| 2013/0312897 A1 | 11/2013 | Vowles | |
| 2014/0067075 A1 | 3/2014 | Makower et al. | |

* cited by examiner

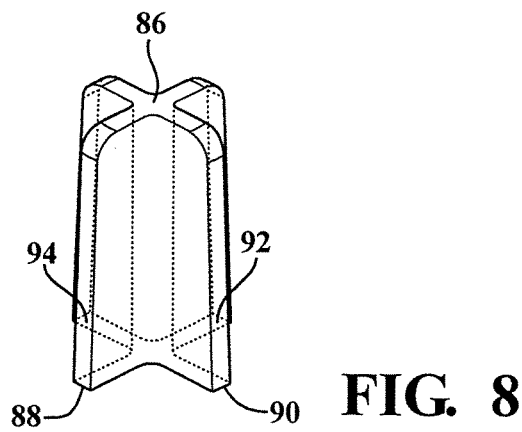
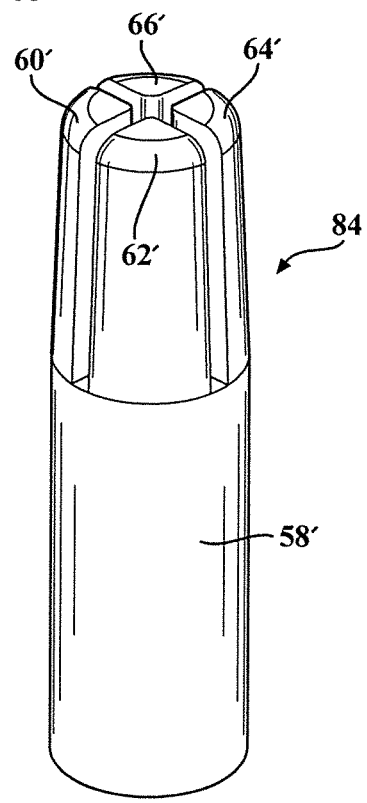
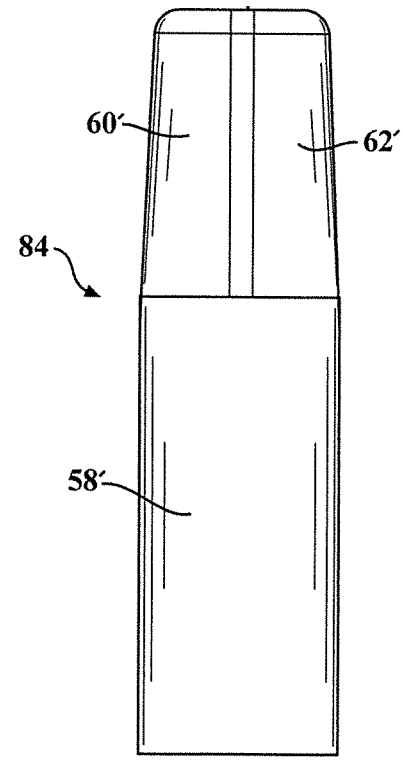
FIG. 8
FIG. 9

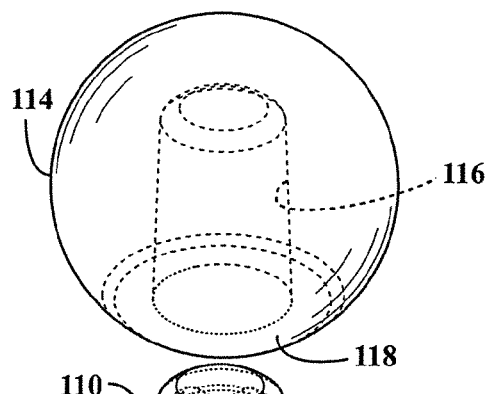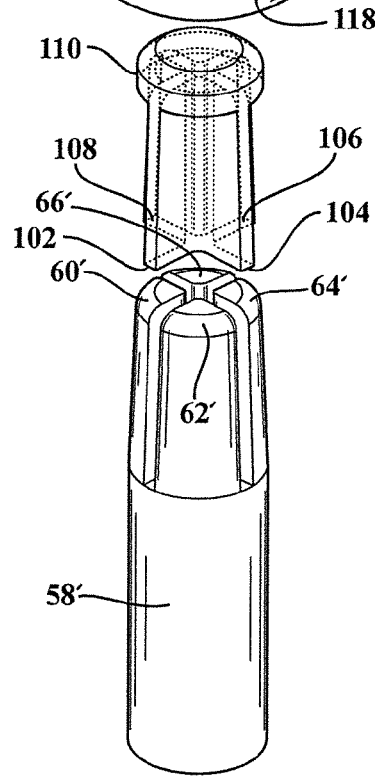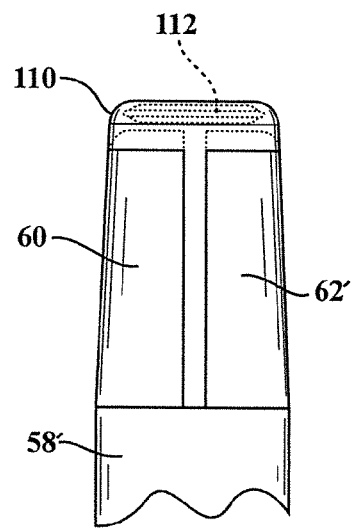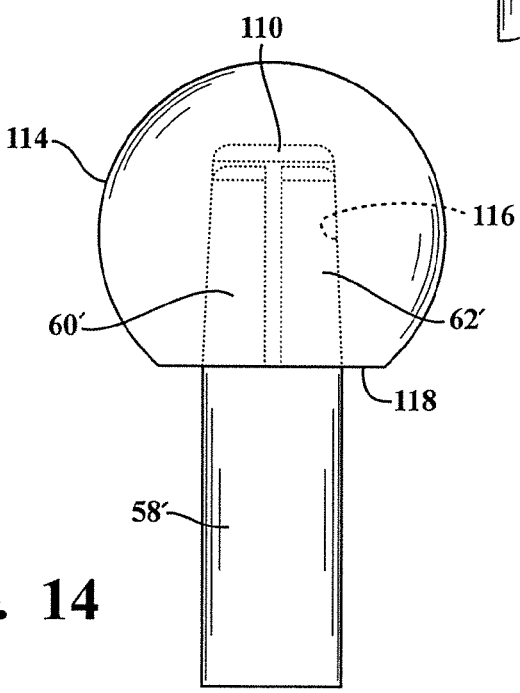

DYNAMIC INTERFACE SUPPORT ESTABLISHED BETWEEN A CERAMIC HIP JOINT BALL AND A SUPPORTING BALL STEM

CROSS-REFERENCE TO RELATED APPLICATIONS

This Application claims the benefit of U.S. Provisional Application 61/825,552 filed on May 21, 2013, the contents of which are incorporated herein in its entirety.

FIELD OF THE INVENTION

The present invention generally relates to a variety of dynamic and force absorbing interfaces established between a hip joint ball and a supporting implant stem and which function to prevent such dynamic forces from fracturing or damaging the hip joint ball. More specifically, the present invention teaches a number of sleeves, caps, or axially installable inserts located at the mounting interface between the hip joint ball and stem implant and in order to absorb and redirect excessive impact forces which might otherwise damage the hip joint ball.

BACKGROUND OF THE INVENTION

The prior art is documented with examples of prosthetic and implant deflection and energy absorbing assemblies. A first example of this is shown in the extra-articular and implantable energy absorbing system of Makower, US 2014/0067075 and which incorporates an elongated and deflectable element extending between joint defining bones.

Clifford, U.S. Pat. No. 7,846,211, teaches a surgical implantation method and device including end-anchored elements and intermediate extending springs for providing energy absorption relative to a patient's anatomy. A similar construction is shown in US 2008/0275564 to Makower et al. and which includes an adjustable energy absorbing device attached to each of first and second support structures anchored to each of the joint defining bones. Reference is also made to the related adjustable energy absorber of U.S. Pat. No. 8,709,090 to Makower et al.

SUMMARY OF THE INVENTION

The present invention discloses an artificial hip joint assembly including a ball mounted atop a supporting stem, the stem adapted to being mounted to a reconditioned end of a femur bone, with the ball adapted to seat within an acetabulum socket of a pelvic bone. An intermediate component is mounted between the ball and stem, the intermediate component incorporating force absorbing and redirecting properties at an engagement interface between the ball and stem in response to impact forces generated upon the ball by the pelvic bone.

The intermediate component can be constructed of a softer material than either the ball or stem, the intermediate component can further include a sleeve exhibiting a plurality of interior threads and facilitating mounting of an exteriorly threaded end location of the stem. Additional features include a groove and slot configuration established between an exterior surface of the sleeve and an interior wall surface of the ball.

The intermediate component can also include a cap affixed over a tapered upper location of the stem. The stem can also exhibit a plurality of upwardly extending, spaced apart and deflectable beams, the component further having a cap exhibiting a plurality of spaced apart and linear extending recesses, the cap nesting between the beams in inter-fitting fashion.

In a further variant, the stem exhibits a plurality of upwardly extending, spaced apart and deflectable beams, the intermediate component further including an "X" cross sectional shaped insert linearly seating between the beams. An end cap element is integrally secured to an upper end face of the "X" cross sectional shaped insert.

A medical grade adhesive can be provided for securing the intermediate component to at least one of the stem and ball. The intermediate component can have at least one of a cylindrical sleeve, tapered, or "X" shaped profile and further comprising a plastic or plastic composite.

Yet additional features include an end cap molded atop the "X" shaped profile and which seats in linearly inserting fashion within and between a plurality of arrayed and spaced apart linear extending beams associated with an integrally formed upper end of the stem. The end cap can also include an accordion like profile for providing a measure of natural cartilage cushioning between the ball and stem.

BRIEF DESCRIPTION OF THE DRAWINGS

Reference will now be made to the attached drawings, when read in combination with the following detailed description, wherein like reference numerals refer to like parts throughout the several views, and in which:

FIGS. 8-9 are exploded and assembled views, respectively, of a fourth variant similar to that depicted in FIGS. 6-7 and in which the cap is reconfigured as an "X" cross-sectional shaped insert which is lengthwise inserted in seating fashion between the spaced and linearly extending beams of the stem support;

FIGS. 12-14 are exploded, semi-assembled and fully assembled views, respectively, of a further modified version of the adaptive and dynamic force absorbing cap such as shown in FIG. 10, and further exhibiting an accordion like or cushioning configuration built into the upper disk portion associated with the "X" cross-sectional shaped profile of the insert, this providing an effect mimicking that of natural cartilage.

DETAILED DESCRIPTION OF THE PREFERRED EMBODIMENTS

Figure 1:
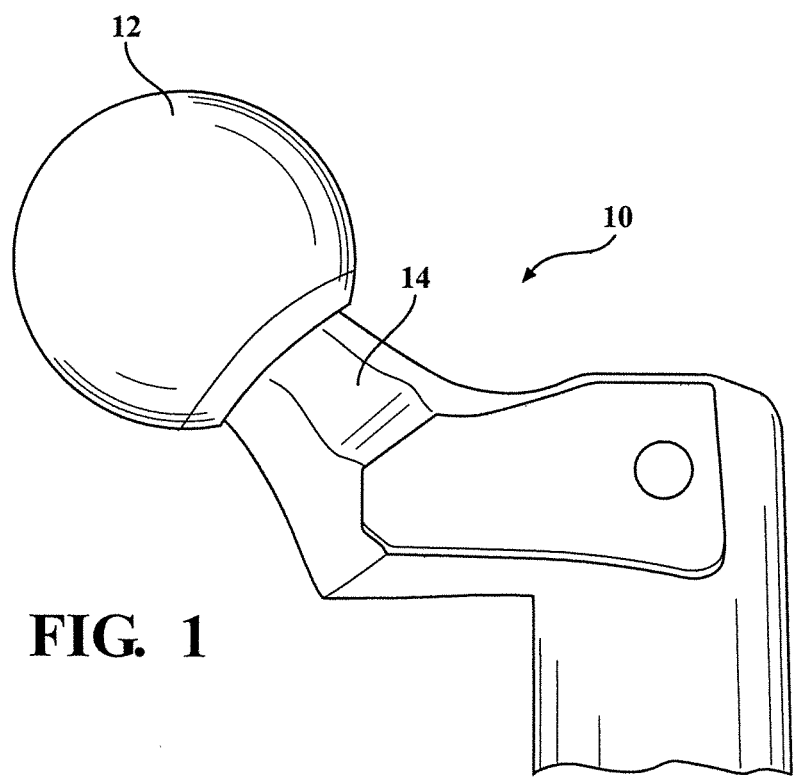
FIG. 1 is an illustration in perspective of a hip joint ball mounted atop a structurally supporting implant stem according to one non-limiting variant of the present invention.

As previously indicated, the present invention discloses a variety of dynamic and force absorbing interfaces established between a hip joint ball and a supporting implant stem and which function to prevent such dynamic forces from fracturing or damaging the hip joint ball. FIG. 1 is an illustration, generally at 10, in perspective of a hip joint ball 12 mounted atop a structurally supporting implant stem 14. Without limitation, the ball 12 can exhibit a ceramic, metallic or other composition and which is typically mounted to durable and metallic stem 14 implanted into such as a reconditioned end of a hip (synovial) joint defining bone.

Figure 1A:
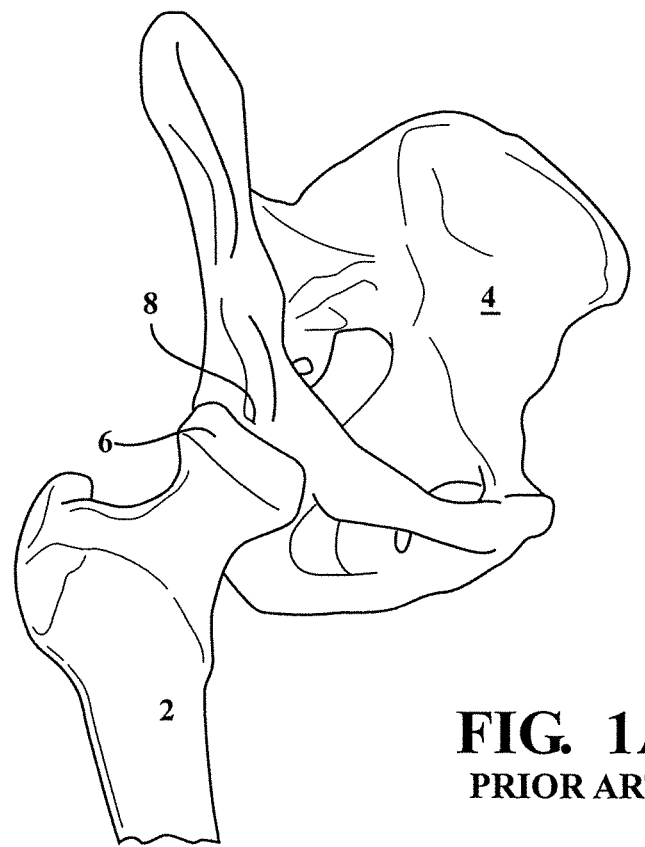
FIG. 1A is an illustration of a natural hip joint established between femur and pelvic bones according to the prior art.

With further reference to the prior art illustration of FIG. 1A, shown is an illustration of a natural hip joint established between femur 2 and pelvic 4 bones. As is known, the hip joint is established between a project upper end (ball) of the femur bone, see natural version at 6 in FIG. 1A, and the concave recessed area of the pelvic bone commonly known as the acetabulum socket, further at 8.

For purposes of clarity of illustration, not depicted such as in FIG. 1A however understood to exist are the collection of supporting architecture for retaining the hip joint, this including each of articular cartridge for connecting the hip ball within the acetabulum socket, along with the other supporting ligaments, cartilage and membranes. The present invention contemplates the use of any combination of natural, artificial or mixture of ligaments and cartilage which can be either retained and/or refashioned or substituted during the in situ implantation process for installing the artificial ball and supporting stem. Also not shown is the reconditioning of the acetabulum socket and which is typically understood to occur during the implantation of the artificial joint.

An artificial hip implant is typically required when the natural bone associated with this joint becomes damaged or otherwise structurally compromised, this often indicated by damage to either or both the upper femur, the pelvic bone or the ligament structure associated with the joint. As is also known, replacement hip joint balls are often constructed of a ceramic, metal or composite material which, while providing a hardened surface needed for functionality and support, has a tendency to crack or fracture. This can in particular be in response to the joint experiencing a sudden or excessive shock force and in which the relatively more fragile hip joint ball tends to become damaged due to the stronger properties of the typically steel constructed stem implant.

Figure 2:
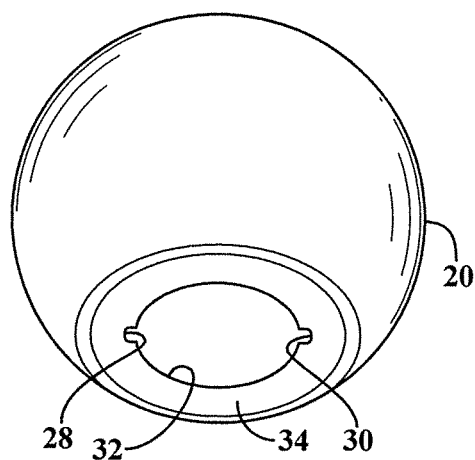
FIG. 2 is an exploded view.
Figure 2:
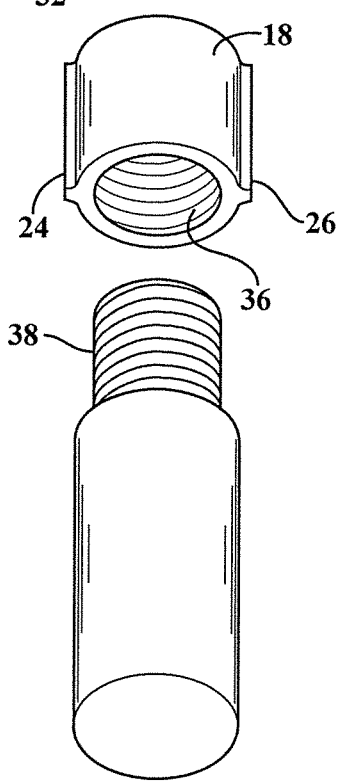
Figure 3:
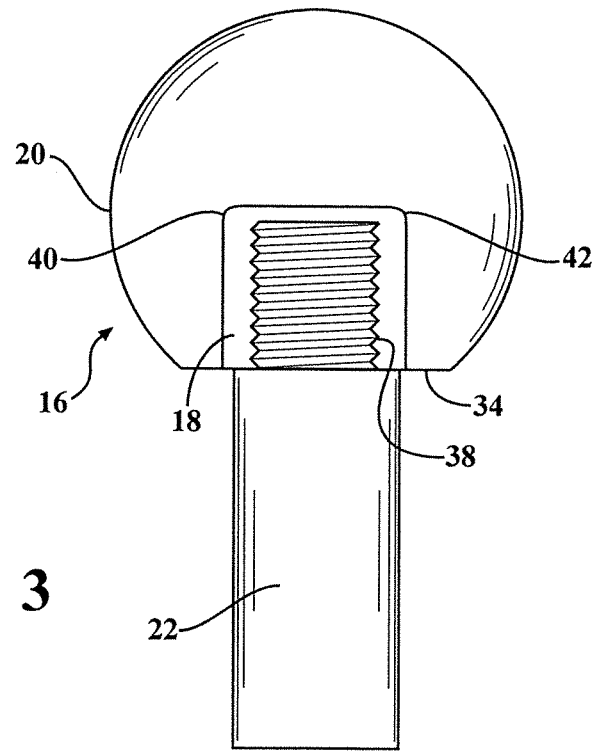
FIG. 3 a cutaway assembled view of a first variant of a ball and stem and which incorporates an intermediate insert sleeve for establishing an even contact surface or profile between the ball and stem, as well as providing force absorptive properties to prevent damage to the ball or mounting interface with the stem.

Given the above explanation, FIG. 2 is an exploded view and FIG. 3 a cutaway assembled view, generally at 16, of a first variant of an artificial and implantable ball and stem (this substituting for the natural ball 6 and femur bone neck support of FIG. 1A which is typically removed in an in-situ operation with the use of a medical saw or the like and prior to the bone end being reconditioned for subsequent implantation of the artificial ball and stem). An intermediate insert sleeve 18 is depicted and establishes an even contact surface or profile between a hip joint ball 20 and a steel stem 22 and which provides force absorptive properties to prevent damage to the ball or mounting interface with the stem. As best shown in FIG. 2, the sleeve 18 is constructed of a suitable metal, plastic or composite material and exhibits any number of exteriorly defined and axially extending protuberances (or grooves) such as shown at 24 and 26, these dimensioned to align with and seat into corresponding axial slots 28 and 30 associated with perimeter edge locations of an inner perimeter extending and underside communicating circular wall 32 associated with the reconfigured hip joint ball 20.

As further shown in FIGS. 2-3, the hip joint ball includes a flat bottom and annular surface profile, at 34, and within which the sleeve 18 is inserted. A medical grade adhesive can also be applied to either or both the exterior of the sleeve 18 or the interior extending circular wall 32 in order to permanently anchor the sleeve 18 as best shown in FIG. 3.

The sleeve 18 also includes a plurality of interior threads, as best shown at 36 in FIG. 2, which facilitate mounting of an exteriorly threaded end location 38 of the stem 22 as shown in FIG. 3. In this manner, the sleeve 18 operates in order to both provide an intermediate interface between the ball 20 and the stem 22 (such as which is established by a pair of annularly spaced boundaries associated with the ball/sleeve and sleeve/stem) for purposes of absorbing, redirecting and/or dispersing impact forces (this also potentially including varying a hardness or durometer rating of the insert to be lesser than that of either the ball or stem) and in order to prevent damage to the hip joint ball. As is also best shown in the cutaway of FIG. 3, the interface boundary established between the exterior of the intermediate sleeve 18 and the inner/underside seating recess of the hip joint ball 20 is minimized (see in particular corners 40 and 42 as well as associated annular side and end face profiles), this in order to minimize the incidence of movement or deflection of the of the hip joint ball 20 relative to the mounting interface established with the stem 22, with resultant incidences of fracture or cracking of the ball 20. Although not further shown, the stem 22 is capable of being anchored into a suitable recess configuration formed during the in-situ operation performed during the reconditioning of the associated end of the femur bone 2

Figure 4:
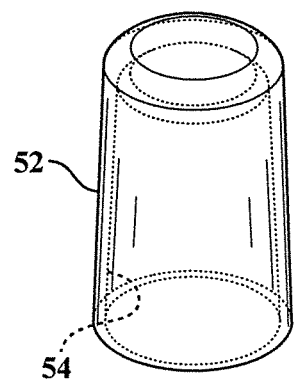
FIGS. 4 and 5 are exploded and assembled views, respectively, of a second variant of a stem support and associated cap of varying durometer or hardness which is softer than that of the supporting stem and in order to provide a dynamic and force-absorptive interface.
Figure 4:
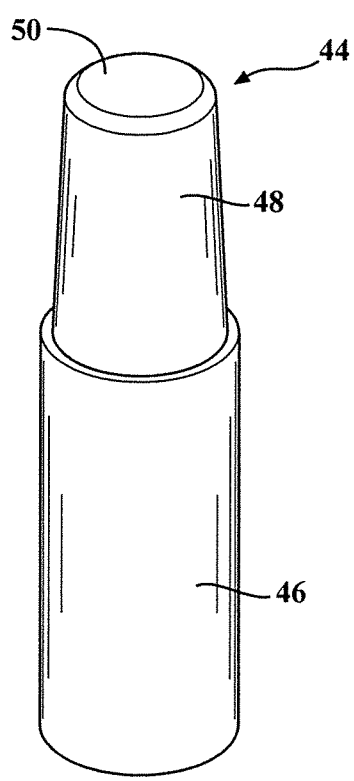
Figure 5:
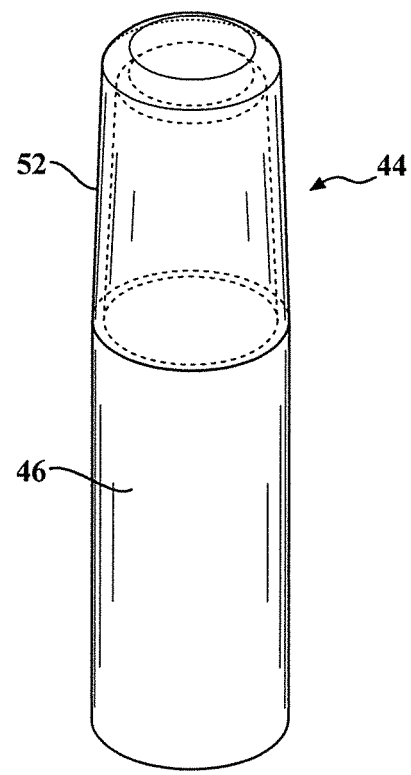

FIGS. 4 and 5 are exploded and assembled views, respectively at 44, of a second variant of a stem support and associated cap of varying durometer or hardness which is softer than that of the supporting stem and in order to provide a dynamic and force-absorptive interface. As shown, the stem includes a cylindrical main body 46 which terminates in an upper and narrowed/tapered, or pseudo-conical, shape 48 with a flat end face 50.

The cap, at 52, exhibits an underside recess configuration, see inner surface at 54, in FIG. 4, which is shaped similar to the conical upper portion 48 of the stem and such that the cap 52 is mounted atop the stem 46 in FIG. 5 again with the use of a medical grade adhesive or the like. As previously described, the cap 52 can be constructed of a softer material (such as having a durometer rating associated with plastics) as compared to either of the stem or hip joint ball (not shown) and in order to provide an even contact or interface boundary between hip joint ball and stem. As with the sleeve 18 in FIG. 2, the cap 52 can also function as an adaptive or dynamic absorbing element for providing cushioning impact in response to jarring forces exerted upon the hip joint ball, and such as which can be transferred to (and dissipated through) the intermediate positioned cap in order to prevent damage to the ball which can otherwise result from impacting the stem at an uneven angle.

Figure 6:
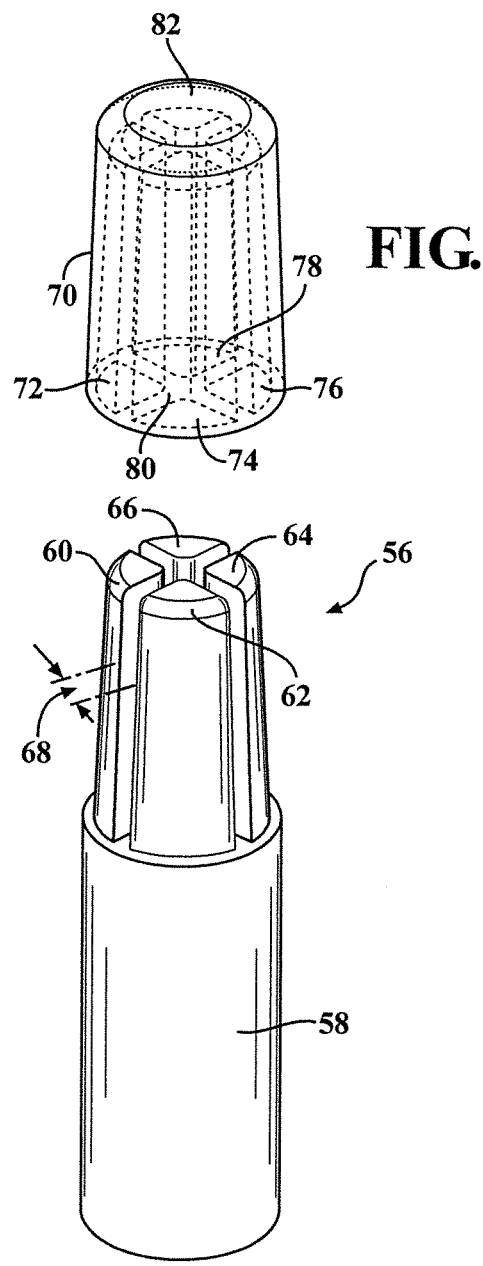
FIGS. 6 and 7 are exploded and assembled views, respectively, of a third variant of a stem support and associated cap which, similar to that shown in FIGS. 4-5, is of a softer durometer rating than the supporting stem, the cap to stem mounting interface exhibiting an inter-seating arrangement of spatially extending and deflectable beams for providing dynamic and force-absorptive support in combination with a mounted hip ball.
Figure 7:
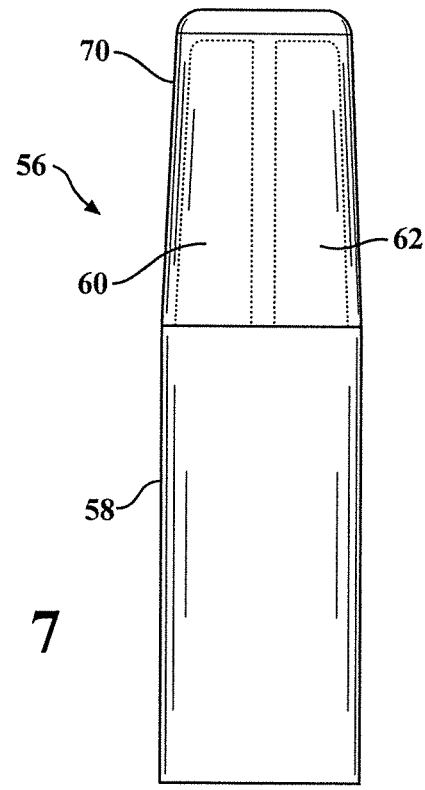

FIGS. 6 and 7 are exploded and assembled views, respectively at 56, of a third variant of a stem support and associated cap which, similar to that shown in FIGS. 4-5. As shown, the stem again includes a cylindrical main body 58 which terminates in a plurality of spatially extending and deflectable beams 60, 62, 64 and 66. As shown, a linear extending gap or spacing is provide between inner opposing surfaces associated with each of the beams 60-66, see selected gap 68 depicted in FIG. 6 between succeeding beams 60 and 62, such that the beams are each capable of being bent or deflected in a number of directions. Consistent with this construction, the stem 58 and integrally configured beams 60-66 can be constructed of a suitable grade spring steel which permits the beams a desired degree of deflection without structurally compromising integrity.

A modification of a softer durometer rated cap is shown at 70, this exhibiting an underside communicating and recessed profile including a plurality of spaced apart and linear extending recesses 72, 74, 76 and 78 (see as best shown in reference to the cap 70 in FIG. 6 shown in partial phantom). A web or like inner connective structure (at 80) establishes the individual recesses 72-78 such that the cap 70 can be mounting upon the stem 58 as shown in FIG. 7 with the individual beams seating within their associated recesses.

Similar to the cap depicted at 52 in FIG. 4, the end cap 70 likewise exhibits a flattened upper end (see at 82) and which, in use, establishes an interface for providing dynamic and force-absorptive support in combination with a mounted hip ball (again not shown). In this fashion, the plastic, composite or other suitably constructed cap 70, in combination with the dynamic and deflectable beams 60-66, provide a force absorptive and redirecting interface for assisting in preventing damage to the underside interior mounting profile established between the hip joint ball and the steel stem 58.

Proceeding to FIGS. 8-9, illustrated are exploded and assembled views, respectively, of a fourth variant similar to that depicted in FIGS. 6-7, with a similarly configured stem 58' including upper most extending and inwardly deflectable beams 60', 62', 64' and 66' (these incrementally differing from the stem 58 of FIG. 6 in that beams extend to the outer joining perimeter of the main cylindrical body 58' as shown), and further in which the cap is reconfigured as shown at 86 to depict an "X" cross-sectional shaped insert constructed of radially projecting and axially extending legs 88, 90, 92 and 94. The sizing of the cap 86, combined with the cross sectional profile of the "X" shaped body, facilitates it being lengthwise inserted in seating fashion between the spaced and linearly extending beams 60-66 of the stem 58 and support. As previously described, a suitable medical adhesive or the like can be employed in order to mount the insert between the beams as shown in FIG. 9 and, in this manner, to establish a desired degree of deflection or give associated with the beams (again by virtue of the softer construction of the insert 86) and in response transferring of impact or shock forces from the surrounding hip joint ball (again not shown)

Figure 10:
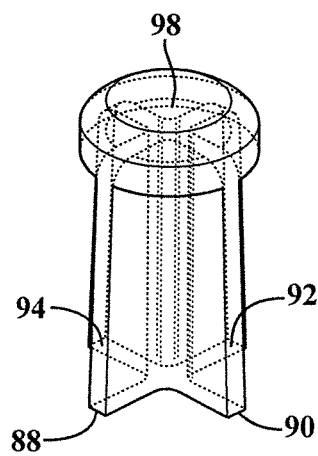
FIGS. 10-11 are exploded and assembled views, respectively, of a yet further redesign of the adaptive and dynamic force absorbing cap combining the "X" cross-sectional shaped profile of FIGS. 8-9 with an end cap element integrally secured to an upper end face of the insert profile.
Figure 10:
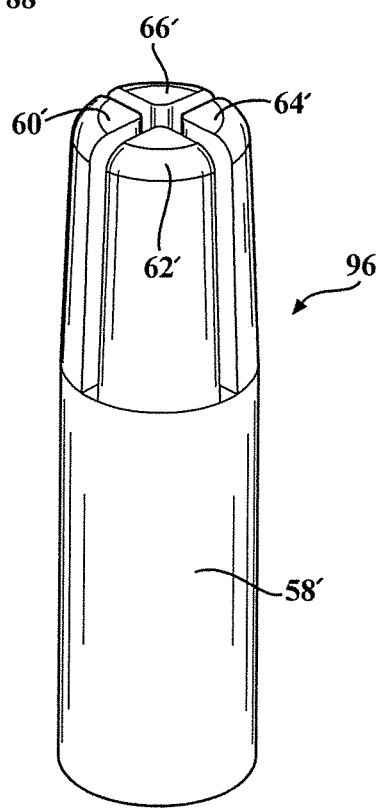
Figure 11:
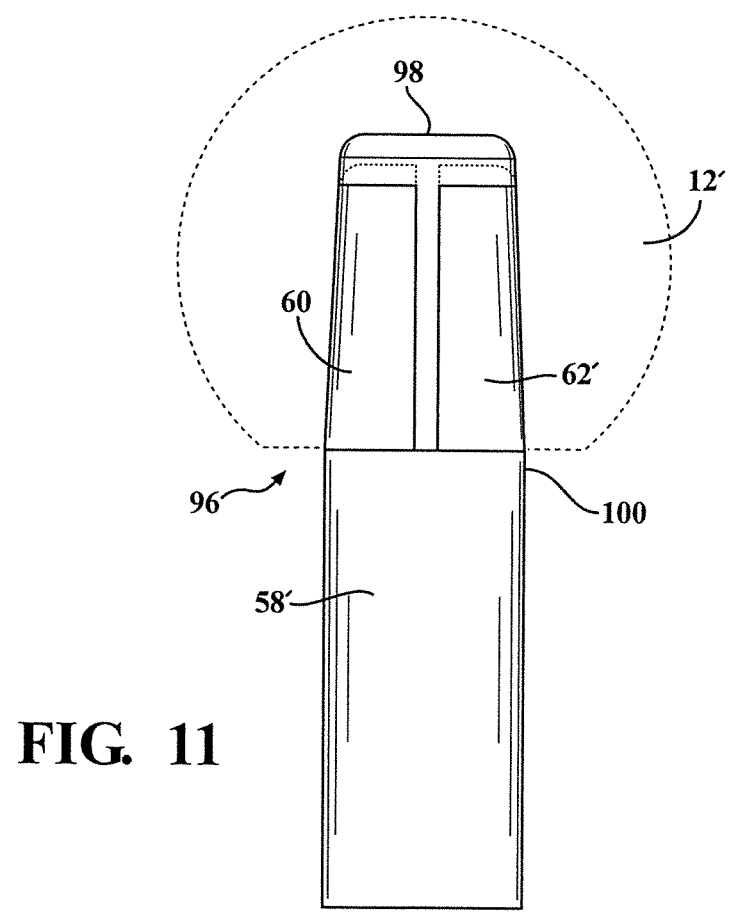

FIGS. 10-11 are exploded and assembled views, respectively at 96, of a yet further variant including an identical stem 58' with beams 62'-66' in combination with a further redesign of the adaptive and dynamic force absorbing cap combining the "X" cross-sectional shaped profile of FIGS. 8-9, including radially projecting and axially extending legs 88, 90, 92 and 94, in combination with an end cap element 98 integrally secured to an upper end face of the insert profile. The combination cap and insert of FIG. 10 installs, as further shown in FIG. 11, to the stem 58' in a lengthwise sliding and keyed fashion and, upon adhesively bonding in place, again provide a degree of deflection and force absorption to facilitate transferring and dissipation of impact forces from a hip joint ball, see as shown at phantom 12' in FIG. 11, installed over the stem 58'.

While not limited to any one particular installation configuration, the hip joint ball 12' is shown mounted to the stem 58' such that a bottom most surface of the ball generally aligns with a lowermost boundary (at 100) established between the deflecting portions of the stem and its main implant portion, this mounting configuration being utilized in each of the individually illustrated embodiments. Without limitation, it is understood that the hip joint ball in each variant can be mounted at any suitable location.

Finally, FIGS. 12-14 are exploded, semi-assembled and fully assembled views, respectively, of a further modified version of an. intermediate inserting component, such as previously shown in FIG. 10 and which in FIGS. 12-14 exhibits a similar arrangement of radially projecting and axially extending legs 102, 104, 106 and 108, in combination with an end cap element 110 integrally secured to an upper end face of the insert profile. The adaptive and dynamic force absorbing cap best shown in FIG. 11 further exhibits an interior accordion-like or cushioning configuration, at 112, incorporated into the upper disk portion, the thickness of which can be designed to provide a cushioning effect similar to that of natural cartilage.

As previously described, a ball 114 is provided and can exhibit a ceramic or other suitable construction such as metal or any composite or variation of materials. An underside profile of the ball includes an interior pseudo-cylindrical and slightly tapered conical profile (see inner wall 116 in partial phantom) which communicates with a flattened annular (bottom) end profile 118. In this fashion, and upon the keyed intermediate insert (such as which exhibits a different durometer plastic as compared to the stem 58') being inserted (and optionally cemented) within and between the beams 62'-66' of the stem, the ball 114 is mounted in the manner depicted in linear cutaway FIG. 14 by sliding downward to seat over the exterior profile defined by the upper stem and "X" cross sectional shaped and linearly seating insert sleeve.

Additional medical grade adhesive can again be provided for cementing the ball over the sleeve/insert interface profile. In this fashion, the sleeve to stem profile established with the hip joint ball functions to both provide shock and force absorption as well as to function in a manner similar to that of natural cartilage, this in order to minimize the likelihood of damage to the ball or stem mounting interface and such as which can result from a shock or impact force resulting from such as the engagement of the pelvic acetabulum socket with the contacting artificial ball.

Having described our invention, other and additional preferred embodiments will become apparent to those skilled in the art to which it pertains, and without deviating from the scope of the appended claims:

We claim:
1. An artificial hip joint assembly, comprising:
a ball mounted atop a supporting stem, said stem adapted to being mounted to a reconditioned end of a femur bone, said ball adapted to seat within an acetabulum socket of a pelvic bone;
an intermediate insert mounted between said ball and stem, said insert having a specified shape and size and being constructed of a softer material than either said ball or stem;
the stem further exhibiting a plurality of upwardly extending, spaced apart and deflectable beams, said insert further exhibiting an "X" cross sectional shape linearly seating between said beams; and
said insert incorporating force absorbing and redirecting properties at an engagement interface between said ball and stem in response to impact forces which may be generated upon said ball by the pelvic bone.

2. The hip joint assembly as described in claim 1, further comprising an end cap element integrally secured to an upper end face of said "X" cross sectional shaped insert.

3. The hip joint assembly as described in claim 1, further comprising a medical grade adhesive for securing said intermediate insert to at least one of said stem and ball.

4. The hip joint assembly as described in claim 1, said insert material being at least one of a plastic or plastic composite material.

5. An artificial hip joint assembly, comprising:
- a ball mounted atop a supporting stem, said stem adapted to being mounted to a reconditioned end of a femur bone, said ball adapted to seat within an acetabulum socket of a pelvic bone;
- an intermediate insert mounted between said ball and stem, said insert incorporating force absorbing and redirecting properties at an engagement interface between said ball and stem in response to impact forces which may be generated upon said ball by the pelvic bone, said insert having a specified shape and size and being constructed of a softer material than either said ball or stem; and
- said stem further exhibiting a plurality of upwardly extending, spaced apart and deflectable beams, said insert exhibiting a cross sectional profile aligning with gaps extending between said beams, enabling said insert to linearly seat between said beams in inter-fitting fashion.

6. The hip joint assembly as described in claim 5, said intermediate insert comprising an "X" cross sectional shape.

7. The hip joint assembly as described in claim 6, said insert comprising at least one of a plastic or plastic composite material.

8. The hip joint assembly as described in claim 5, further comprising an end cap element integrally secured to an upper end face of said insert.

9. The hip joint assembly as described in claim 5, further comprising a medical grade adhesive for securing said insert to at least one of said stem and ball.

* * * * *